(12) United States Patent
Fesik et al.

(10) Patent No.: US 6,897,337 B2
(45) Date of Patent: May 24, 2005

(54) SITE-SPECIFIC ISOTOPICALLY-LABELED PROTEINS, AMINO ACIDS, AND BIOCHEMICAL PRECURSORS THEREFOR

(75) Inventors: Stephen W. Fesik, Gurnee, IL (US); David J. Augeri, Emerson, NJ (US)

(73) Assignee: Abbott Laboratories, Abbott Park, IL (US)

( * ) Notice: Subject to any disclaimer, the term of this patent is extended or adjusted under 35 U.S.C. 154(b) by 345 days.

(21) Appl. No.: 10/138,620

(22) Filed: May 3, 2002

(65) Prior Publication Data

US 2004/0086938 A1 May 6, 2004

Related U.S. Application Data

(62) Division of application No. 09/544,620, filed on Apr. 6, 2000, now abandoned.
(60) Provisional application No. 60/128,668, filed on Apr. 9, 1999.

(51) Int. Cl.$^7$ .............................................. C07C 229/00
(52) U.S. Cl. ..................................... 562/575; 562/577
(58) Field of Search .................................. 562/575, 577

(56) References Cited

U.S. PATENT DOCUMENTS 5,698,401 A   12/1997 Fesik et al.
5,804,390 A    9/1998 Fesik et al.

OTHER PUBLICATIONS

Bonner, W.A., "Beta radiolysis of crystalline 14C–labeled amino acids" Journal of Organic Chemistry 43(3):522–524 (1978).
Crout, D.H. "Pyrrolizidine alkaloids. The bioynthesis of senecic acid" Journal of the Chemical Society, Perkin Transactions 1, 1972, pp. 671–680.
Neri, D., "Stereospecific nuclear magnetic resonance assignments of the methyl groups of valine and leucine in the DNA–binding domain of the 434 repressor by biosynthetically directed fractional 13C labeling" Biochemistry 28(19):7510–7516 (1989).
LeMaster, D.M., et al., "Biosynthetic Production of 13C–Labeled Amino Acids with Site Specific Enrichment," J. Biol. Chem, 257(3): 1224–1230 (1987).
Nicholson, L.K. et al., "Dynamics of Methyl Groups in Proteins as Studied by Proton Detected 13C NMR Spectroscopy," Biochemistry, 31(23): 5253–5263 (1992).
Schwenk, W.F., "Recycling of an Amino Acid Label with Prolonged Isotope Infusion: Implications for Kinetic Studies," Am. J. Physiol., 248 (Part 1), E482–E487 (1985).
XP–002146814 CAS Registry Handbook.
American Chemical Society Handbook Number Section, 1988 Supplement, p. 2456RQ—col. 1 (1988).
Ye, Q–Z., et al., "Purification and Characterization of the Human Stromelysin Catalytic Domain Expressed in *Escherichia coli* ", *Biochemistry*, 31:11231–11235 (1992).

*Primary Examiner*—Paul J. Killos
(74) *Attorney, Agent, or Firm*—Dianne Casuto

(57) ABSTRACT

Site-specific isotopically-labeled valine, leucine, and isoleucine and biosynthetic precursors for these amino acids are provided. The amino acids are labeled with $^{13}C$ or $^{14}C$ at the methyl group carbon atom(s) most remote from the carboxyl group. Also disclosed are the biochemical precursors of these labeled amino acids, 2-keto-4-($^n$C)butyric acid and 2-keto-3-($^n$C-methyl)-4-($^n$C)-butyric acid in which n, at each occurrence, is 13 or 14.

Also disclosed are proteins, protein fragments, and polypeptides containing these site-specifically isotopically labeled amino acids, and methods for preparing the biochemical precursors, the amino acids, and the proteins, protein fragments, and polypeptides.

7 Claims, No Drawings

SITE-SPECIFIC ISOTOPICALLY-LABELED PROTEINS, AMINO ACIDS, AND BIOCHEMICAL PRECURSORS THEREFOR

This application is a Division of Ser. No. 09/544,620 filed on Apr. 6, 2000 now abandoned and an original conversion from the provisional application Ser. No. 60/128,668, filed Apr. 9, 1999.

FIELD OF THE INVENTION

The present invention relates to site-specific isotopically-labeled organic compounds and processes for their preparation. More particularly, the present invention concerns site-specific isotopically-labeled biochemical precursors of leucine, isoleucine, and valine, the isotopically-labeled amino acids per se, proteins, protein fragments or polypeptides made therefrom, and related methods of preparation.

BACKGROUND OF THE INVENTION

A recently-developed technique for discovering new drug leads involves the use of nuclear magnetic resonance (NMR) spectroscopy to discover compounds that bind to a particular target molecule such as a protein (see, for example, U.S. Pat. Nos. 5,698,401 and 5,804,390, to Fesik, et al.). The technique involves the determination of a first two-dimensional $^{15}N/^1H$ NMR correlation spectrum of a protein in which nitrogen atom sites have been isotopically enriched with $^{15}N$. This first correlation spectrum is obtained for the protein in the absence of any potential ligand compound(s). Next a suspected ligand compound, or a mixture of such putative ligand compounds, is mixed with the isotopically enriched protein, and a second NMR correlation spectrum is obtained. The two spectra are compared, and differences between the two spectra provide information about 1) the existence of binding between any ligand and the host protein, 2) the site(s) of binding, and 3) the strength(s) of binding.

The technique described in Fesik, et al., supra, employs target molecules which have been isotopically enriched with the NMR-detectable $^{15}N$ spin nucleus. This method relies upon the genetic modification of a suitable microorganism to express the desired protein, protein fragment, or polypeptide, followed by culturing the modified microorganism in a nutrient medium containing assimilable sources of carbon and nitrogen which include $^{15}N$-labeled nutrients. Comparatively inexpensive commercially available $^{15}N$ ammonium salts provided the $^{15}N$ source.

However, the application of this NMR drug discovery technique to target molecules isotopically enriched with $^{13}C$ has been hampered by two drawbacks. First, it is comparatively expensive to produce $^{13}C$-enriched target molecules in any useful quantities. For example, the production of proteins by genetically modified microorganisms grown in nutrient media containing commercially available uniformly-labeled glucose (glucose-$^{13}C_6$) is expensive. At the time of filing this application, the cost of glucose-$^{13}C_6$ was approximately $480/g. Alternatively, the production of $^{13}C$-labeled proteins by including uniformly $^{13}C$-labeled amino acids in the nutrient medium is similarly expensive. Second, the biomolecules produced using glucose-$^{13}C_6$ or commercially available uniformly $^{13}C$-enriched amino acids are not ideally suited for the NMR correlation spectra technique. Biomolecules expressed by microorganisms grown in nutrient media containing uniformly $^{13}C$-enriched starting materials contain adjacent $^{13}C$-labeled carbon atoms. Since the NMR technique depends upon detection of spatial spin coupling (i.e., the nuclear Overhauser effect), the relatively strong spin-spin coupling of adjacent $^{13}C$ nuclei interferes with the desired observation. There is thus a need for the development of site-specifically $^{13}C$-enriched amino acids, proteins and polypeptides.

SUMMARY OF THE INVENTION

The instant invention provides biochemical precursors of the site-specific isotopically-enriched amino acids leucine, isoleucine, and valine, as well as the site-specific isotopically-enriched amino acids per se. Additionally, proteins, protein fragments and polypeptides containing site-specific isotopically-enriched aminoacyl residues derived from these amino acids, and methods for their production, are also provided. The amino acids and the amino acid biosynthetic precursors are isotopically enriched with either $^{13}C$ or $^{14}C$ at the carbon atoms of methyl groups most remote from their carboxyl group. In the labeled amino acids of the present invention, non-adjacent carbon atoms are labeled. In the case where the label is $^{13}C$, the amino acids of this invention are thus ideally suited for use in the NM drug discovery technique, since there is no interference with the desired signals by adjacent atom $^{13}C$-$^{13}C$ spin-spin interaction. Moreover, since the amino acids are labeled only at methyl groups, the three magnetically equivalent hydrogen atoms of the methyl group(s) provide strong NMR signals for observation of any effects of coupling with the $^{13}C$ atom(s) to which they are attached.

Specifically, the present invention provides compounds of formula I

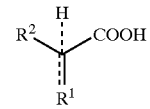

or a salt thereof, wherein $R^1$ is oxygen or $NH_2$, and $R^2$ is selected from the group consisting of

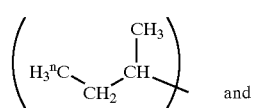

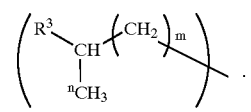

In the formulae presented above, $R^3$ is hydrogen or $^nCH_3$, the dotted line bonds represent valence bonds, m is zero or one, and n, at each occurrence, is 13 or 14, with the provisos that: a) when $R^1$ is $NH_2$, the second valence bond represented by the dotted line bond to $R^1$ is absent and the hydrogen attached to the dotted line bond is present; b) when $R^1$ is oxygen, the second valence bond represented by the dotted line bond to $R^1$ is present and the hydrogen atom attached to the dotted line bond is absent; c) when $R^1$ is oxygen, $R^2$ is B and m is zero; and d) when $R^1$ is $NH_2$, $R^3$ is hydrogen or $^nCH_3$.

The present invention provides the site-specific $^{13}C$- and $^{14}C$-enriched amino acids isoleucine (formula I above where $R^1$ is amino, $R^2$ is A); leucine (formula I above where $R^3$ is amino, $R^2$ is B, $R^3$ is $^nCH_3$, and m is one), and valine (formula I above where $R^1$ is amino, $R^2$ is B, $R^3$ is $^nCH_3$, and m is zero), and the site-specific $^{13}$C- and $^{14}$C-enriched biochemical precursors of these amino acids, 2-keto-4-($^n$C)-butyric acid (formula I above where $R^1$ is oxygen, $R^2$ is B, m is zero, and $R^3$ is hydrogen) and 2-keto-3-($^n$C-methyl)-4-($^n$C)-butyric acid (formula I above where $R^1$ is oxygen, $R^2$ is B, m is zero, and $R^3$ is $^n$CH$_3$). In the foregoing, n represents either 13 (i.e., $^{13}$C-enriched compounds) or 14 (i.e., $^{14}$C-enriched compounds).

The present invention further provides proteins, protein fragments, and polypeptides containing aminoacyl residues derived from one or more of the amino acids selected from the group consisting of L-2-amino-3-methyl-5-($^{13}$C)-pentanoic acid; L-2-amino-3-methyl-5-($^{14}$C)-pentanoic acid; L-2-amino-4-($^{13}$C-methyl-5-($^{13}$C)-pentanoic; L-2-amino-4-($^{14}$C-methyl-5-($^{14}$C)-pentanoic acid; L-2-amino-3-($^{13}$C-methyl)-5-($^{13}$C)-butanoic acid; and L-2-amino-3-($^{14}$C methyl)-5-($^{14}$C)-butanoic acid.

Also provided by the present invention are chemical methods of preparing the site-specific $^{13}$C- and $^{14}$C-labeled biochemical precursors acids, 2-keto-4-($^n$C)-butyric acid and 3-($^n$C-methyl)-4-($^n$C)-butyric acid, or salts thereof, which involves reacting a compound of formula IV

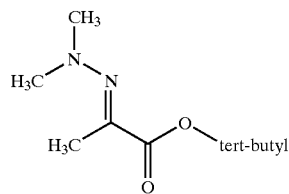

IV with isotopically-labeled methyl iodide (H$_3$$^n$CI) to produce a compound of formula V

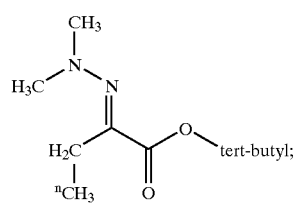

V removing the protecting tert-butyl ester and dimethylhydrazino groups of a compound of formula V to produce 2-keto-4-($^n$C)-butyric acid; or further reacting a compound of formula V with isotopically-labeled methyl iodide (H$_3$$^n$CI) where n is 13 or 14, to produce a compound of formula VI

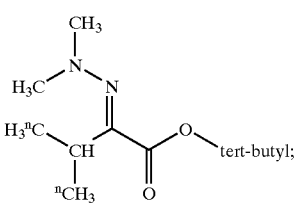

VI removing the protecting tert-butyl ester and dimethylhydrazino groups to produce 2-keto-3-($^n$C-methyl)-4-($^n$C)-butyric acid; and optionally salifying the products.

The present invention additionally provides methods for preparing the site-specific $^{13}$C- and $^{14}$C-labeled amino acids, leucine, isoleucine, and valine. The process involves genetically modifying a microorganism to express a polypeptide containing an amino acid selected from leucine, isoleucine, valine and mixtures thereof; culturing the modified microorganism in a nutrient medium containing assimilable sources of carbon and nitrogen which includes 2-keto-4-($^n$C)-butyric acid, 2-keto-3-($^n$C-methyl)-4-($^n$C)-butyric acid, and salts and mixtures thereof; isolating the resulting expressed polypeptide; and fragmenting the polypeptide and isolating the individual amino acids. The expressed polypeptide is fragmented by conventional methods known in the art including hydrolysis or enzymatic cleavage.

The yield of a particular amino acid may be maximized and the cost minimized by modifying the host microorganism to express a homopolymer of the amino acid, and utilizing the appropriate isotopically enriched biosynthetic precursor in the nutrient medium.

The present invention still further provides a method of preparing a protein, protein fragment, or polypeptide containing amino acyl residues derived from amino acids selected from the group consisting of L-2-amino-3-methyl-5-($^{13}$C)-pentanoic acid; L-2-amino-3-methyl-5-($^{14}$C)-pentanoic acid; L-2-amino-4-($^{13}$C-methyl-5-($^{13}$C)-pentanoic; L-2-amino-4-($^{14}$C-methyl-5-($^{14}$C)-pentanoic acid; L-2-amino-3-($^{13}$C-methyl)-5-($^{13}$C)-butanoic acid; and L-2-amino-3-($^{14}$C-methyl)-5-($^{14}$C)-butanoic acid which involves genetically modifying a microorganism to express a pre-determined protein, protein fragment or polypeptide; culturing the modified microorganism in a nutrient medium containing assimilable sources of carbon and nitrogen which includes 2-keto-4-($^n$C)-butyric acid, 2-keto-3-($^n$C-methyl)-4-($^n$C)-butyric acid, and salts and mixtures thereof; and isolating the resulting expressed polypeptide.

DETAILED DESCRIPTION OF THE INVENTION

The natural isotopic abundance of $^{13}$C is 1.11%, and that of $^{14}$C is negligibly low. Thus the probability that any given carbon atom within an organic molecule is $^{13}$C is normally about 0.0111, and the probability that any given carbon atom is $^{14}$C is quite low. When target proteins are prepared for use in the adapted NMR "screening" or drug discovery process as described by Fesik, et al., supra, it is desirable that the $^{13}$C NMR signal be enhanced by increasing the natural $^{13}$C content of the target molecule being studied. This is accomplished by either uniformly or selectively enriching the target molecule with $^{13}$C. As used throughout this specification and the appended claims, the terms "uniform enrichment," "uniformly enriching," "uniformly enriched," uniform labeling" and "uniformly labeled" mean increasing to a value greater than 0.0111, by synthetic means, the probability that a carbon atom randomly selected throughout the target molecule will be $^{13}$C. The terms "specific enrichment," "site-specific enrichment," "specifically enriching," "specifically enriched," "specifically labeling" and "specifically labeled" mean increasing to a value greater than 0.0111, by synthetic means, the probability that carbon atoms at one or more specific pre-selected site(s) within the target molecule will be $^{13}$C.

For example, biomolecules expressed by genetically modified microorganisms grown in a nutrient medium containing uniformly $^{13}$C-enriched glucose will be uniformly $^{13}$C enriched. A protein expressed by a genetically modified microorganism grown in a nutrient medium containing an amino acid which is $^{13}$C-enriched only on the methyl side chain would be specifically enriched by $^{13}$C at the alanyl residues contained within the expressed protein. Similarly, proteins expressed by the method of this invention will be site-specifically enriched by $^{13}C$ or $^{14}C$ at the side-chain terminal methyl groups of leucine, isoleucine, and valine.

The method of the present invention also permits the preparation of site-specifically labeled leucine, isoleucine and valine, proteins, protein fragments, or polypeptides made from these labeled amino acids, and the amino acid biosynthetic precursors with labeled with $^{14}C$ as well as $^{13}C$. Such compounds are useful, for example, in studies of protein metabolism where it is desirable to follow the course and fate of protein degradation by radiometric methods.

Further terms used throughout this specification and the appended claims have their usually accepted meanings. The following specific terms have the ascribed meanings:

"DTT" means dithiothreitol.

"HEPES" denotes N-2-hydroxyethylpiperazine-N'-2-ethylsulfonic acid.

"IPTG" means isopropyl-β-D-thiogalactopyranoside.

"PMSF" refers to α-toluenesulfonyl fluoride.

"SCD" refers to the catalytic domain (residues 81–256) of stromelysin.

The preparation of an exemplary site-specific $^nC$-enriched protein fragment target molecule is set forth below. The particular example shown demonstrates the preparation of the so-called "catalytic domain" of human stromelysin ("SCD"), labeled with site-specific $^{13}C$-enriched leucine, valine, and isoleucine. While shown with $^{13}C$-labeled amino acid precursors, the method is equally applicable starting with $^{14}C$-labeled amino acid precursors. A preferred means of preparing adequate quantities of specifically $^nC$-enriched polypeptide-containing target molecules involves the transformation of a host cell with an expression vector containing a polynucleotide encoding the desired polypeptide. The protein or polypeptide protein fragment is expressed by culturing the transformed cell line in a medium containing assimilable sources of carbon and nitrogen well known in the art and including the $^nC$-enriched biochemical precursors of this invention. For site-specific labeling of the protein or protein fragment in accordance with the present invention, assimilable sources for $^nC$. labeling of a target polypeptide include $^nC$-labeled biosynthetic precursors of amino acids.

For example, it is known that α-keto-butyrate is the biosynthetic precursor of isoleucine, and that α-keto-isovalerate is the biosynthetic precursor of both valine and leucine. Scheme I below shows how the specifically $^nC$-enriched biosynthetic precursors of leucine, isoleucine, and valine can be synthesized. The Scheme employs the comparatively inexpensive $^nC$-enriched methyl iodide, $H_3^nCI$, as the source for isotopic enrichment to produce $^nC$-terminally-labeled α-keto-butyric acid and α-keto-isovaleric acid.

The use of a uniformly $^{13}C$-enriched nutrient such as glucose-$^{13}C_6$ has been typically used as a convenient means of introducing $^{13}C$ enrichment into a target compound; however, it is very expensive. Furthermore, a vast majority of the carbon sites in uniformly $^{13}C$-labeled targets will have a covalently bonded neighbor which is also $^{13}C$-labeled, introducing $^{13}C$-$^{13}C$ coupling which can negatively impact both the signal-to-noise and the relaxation properties of $^{13}C$-labeled sites in the target biomolecule. Alternatively, the nutrient medium may include commercially available uniformly $^{13}C$-labeled amino acids. While this technique reduces the "dilution" of the labeling, it too, is a costly alternative and likewise suffers from the drawback of adjacent carbon atom $^{13}C$-$^{13}C$ spin-spin interactions.

However, the method of the present invention for $^nC$-labeling of a polypeptide target molecule comprises growing the genetically modified cell line in a nutrient medium containing $^nC$-labeled biosynthetic precursors of particular amino acids. Not only are certain of the amino acids in the resulting protein, protein fragment or polypeptide isotopically enriched, those amino acids are site-specifically labeled.

In a method of one embodiment of the invention, preferred amino acid precursors are labeled α-keto-butyric acid and α-keto-isovaleric acid. The biosynthetic products of these precursors are leucine, isoleucine, and valine, in which particular side-chain methyl groups are $^nC$-enriched. Because the methyl groups each have three hydrogen atoms connected to a $^nC$-labeled carbon atom, when n is 13, the corresponding NMR signals are particularly strong and distinctive.

The synthesis for labeled α-keto-butyric acid and α-keto-isovaleric acid involves the C-methylation of the terminal carbon atom in pyruvic acid with $^nC$-enriched methyl iodide. Normally, the alkylation of α-keto acids such as pyruvate is inherently difficult and is accompanied by decomposition of the enolate intermediate with the formation of numerous side products. However, Spencer, et al., *Tetrahedron Letters,* 1975, 3889 and Williams, et al., ibid., 1990, 5881 have shown that alkylation of the corresponding oxime enolate has been carried out, although alkylation with primary electrophiles (for example, methyl iodide) was problematic. D. Enders, et al., *Angew. Chem. Int. Eng. Ed.,* 1992, 618 and D. Enders, et al., *Synlett,* 1992, 901 have demonstrated that alkylation of an N,N-dimethylhydrazone of pyruvate is possible, but specifically mentioned that the bulky 2,6-dialkyl phenyl ester was necessary to prevent self acylation.

Representative compounds of the present invention include the following:

2-keto-4-($^{13}C$)-butyric acid or a salt thereof;

2-keto-4-($^{14}C$)-butyric acid or a salt thereof;

2-keto-3-($^{13}C$-methyl)-4-($^{13}C$)-butyric acid or a salt thereof;

2-keto-3-($^{14}C$-methyl)-4-($^{14}C$)-butyric acid or a salt thereof;

L-2-amino-3-methyl-5-($^{13}C$)-pentanoic acid or a salt thereof;

L-2-amino-3-methyl-5-($^{14}C$)-pentanoic acid or a salt thereof;

L-2-amino-4-($^{13}C$-methyl)-5-($^{13}C$)-pentanoic acid or a salt thereof;

L-2-amino-4-($^{14}C$-methyl)-5-($^{14}C$)-pentanoic acid or a salt thereof;

L-2-amino-3-($^{13}C$-methyl)-5-($^{13}C$)-butanoic acid or a salt thereof; and

L-2-amino-3-($^{14}C$-methyl)-5-($^{14}C$)-butanoic acid or a salt thereof.

The present invention additionally encompasses proteins, protein fragments, and polypeptides containing the site-specific isotopically enriched amino acids L-2-amino-3-methyl-5-($^{13}C$)-pentanoic acid; L-2-amino-3-methyl-5-($^{14}C$)-pentanoic acid; L-2-amino-4-($^{13}C$-methyl)-5-($^{13}C$)-pentanoic; L-2-amino-4-($^{14}C$-methyl)-5-($^{14}C$)-pentanoic acid; L-2-amino-3-($^{13}C$-methyl)-5-($^{13}C$)-butanoic acid; and L-2-amino-3-($^{14}C$-methyl)-5-($^{14}C$)-butanoic acid.

Although the specific compounds named above have been designated as having $^{13}C$- or $^{14}C$-isotopes at specific sites in the compound, it will be understood by those of ordinary skill in the art that the carbon atoms at these sites in the compounds will not be completely $^{13}C$ or $^{14}C$ labeled. The degree of isotopic substitution or "enrichment" at each molecular site depends upon the corresponding degree of enrichment contained in the starting materials utilized in the synthesis.

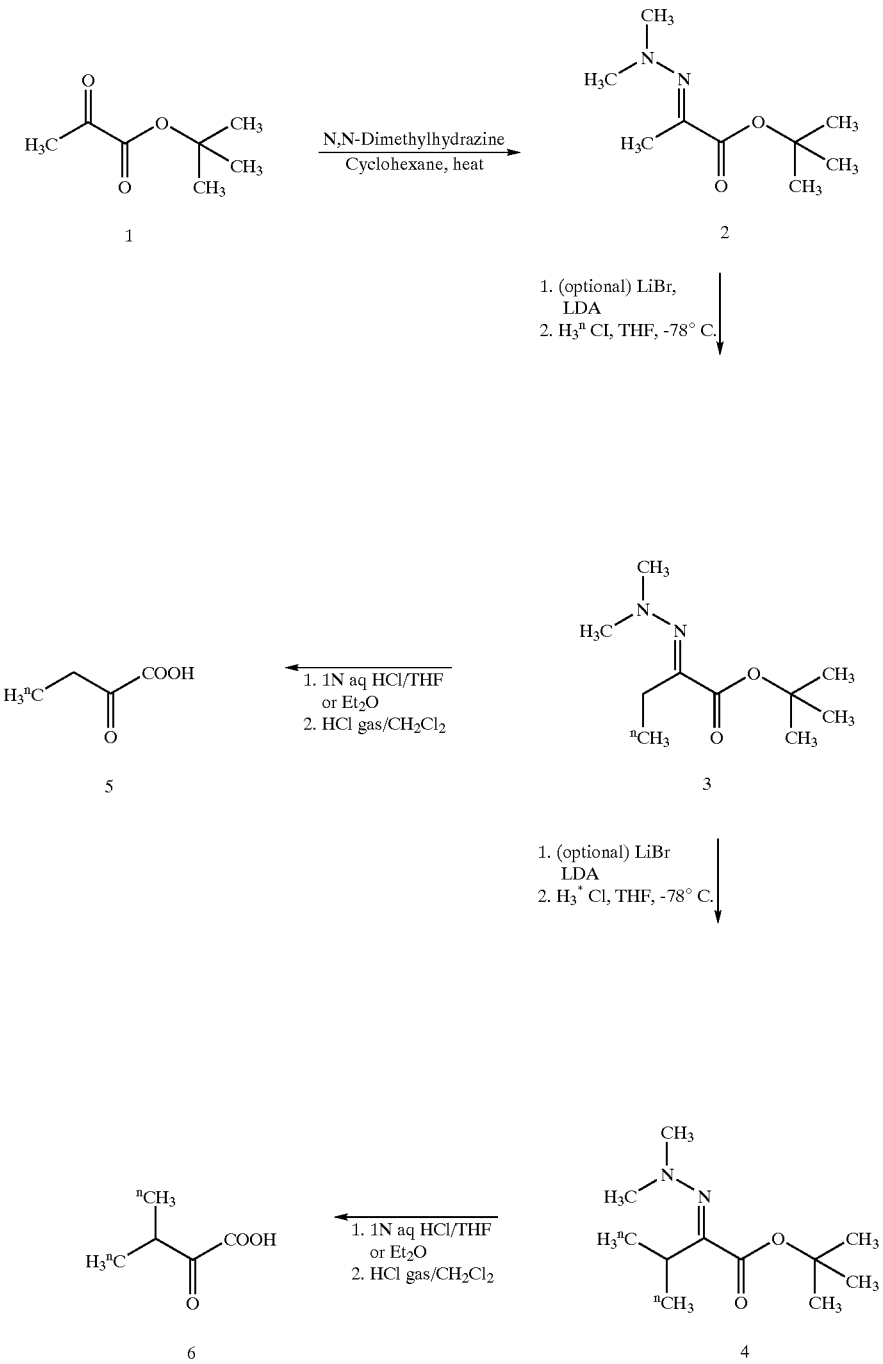

Scheme I
Chemical Synthesis of Labeled Precursors

In Scheme I, tert-butyl pyruvate, 1, is converted to the corresponding N,N-dimethylhydrazone, 2, by reaction with N,N-dimethylhydrazine in diethyl ether at room temperature. The resulting hydrazone, 2, is cooled in a tetrahydrofuran solution to −78° C., and treated with lithium bromide, followed by lithium diisopropylamide to form the intermediate aza-allyl enolate. The enolate is alkylated with $^n$C-labeled methyl iodide to produce hydrazone 3. A second course of alkylation of 3 produces the labeled dimethylated hydrazone, 4. Treatment of 3 and 4 first with aqueous 1N HCl in tetrahydrofuran or diethyl ether (to remove hydrazone) followed by treatment with hydrogen chloride gas in methylene chloride (to remove the t-butyl ester) gives the corresponding $^n$C-terminally labeled α-ketoacids, 5 and 6. Schemes II, III, and IV illustrate, respectively, how these α-ketoacids are biosynthetically converted into $^n$C-leucine, isoleucine and valine. In all of the Schemes, the site(s) of isotopic enrichment are indicated by asterisks.

Scheme II
Biochemical Synthesis of Labeled Isoleucine
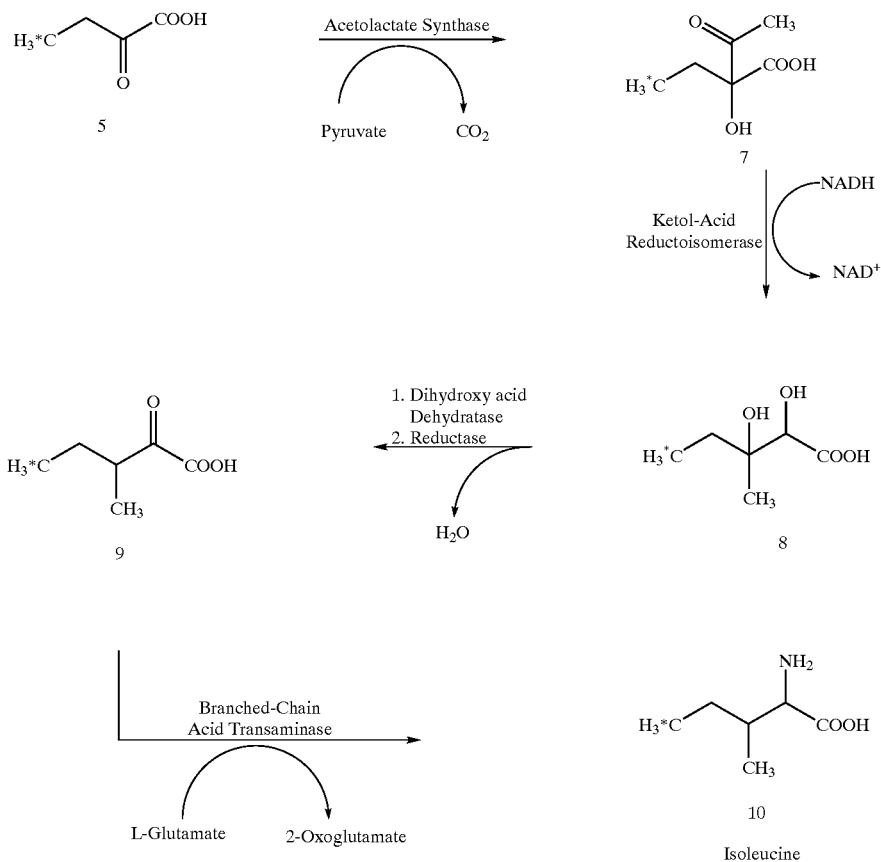
Scheme III
Biochemical Synthesis of Labeled Leucine
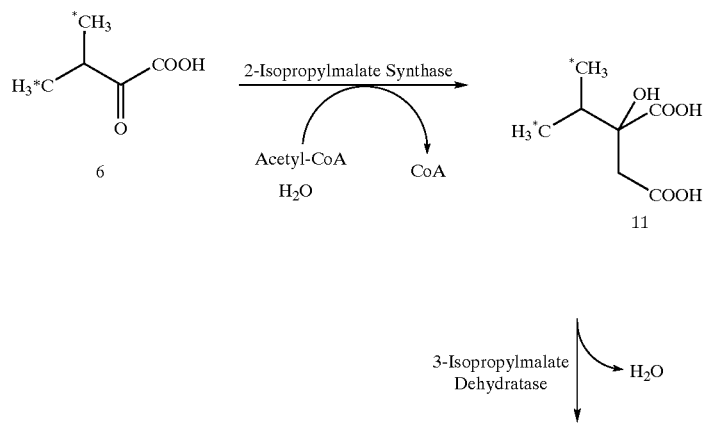

-continued

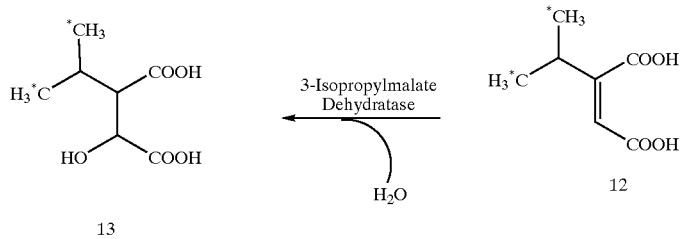

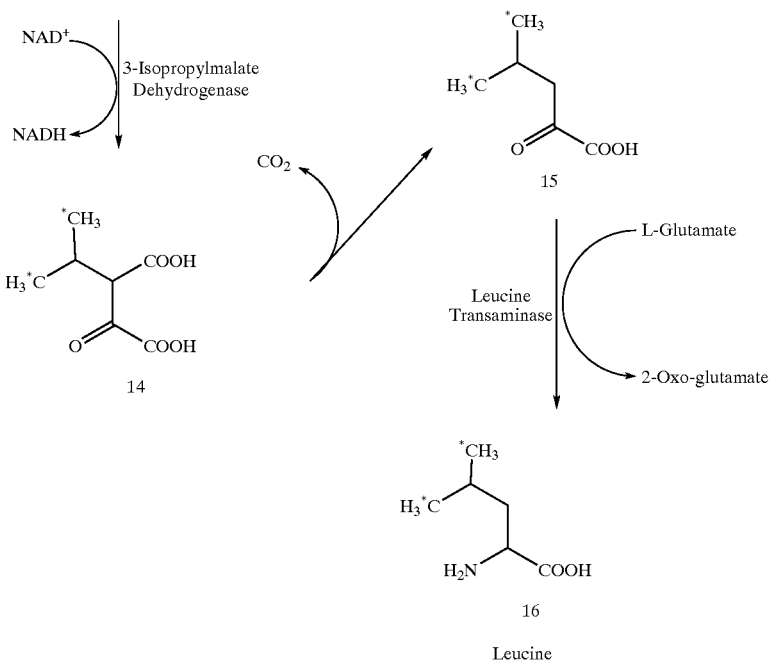

Scheme IV
Biochemical Synthesis of Valine

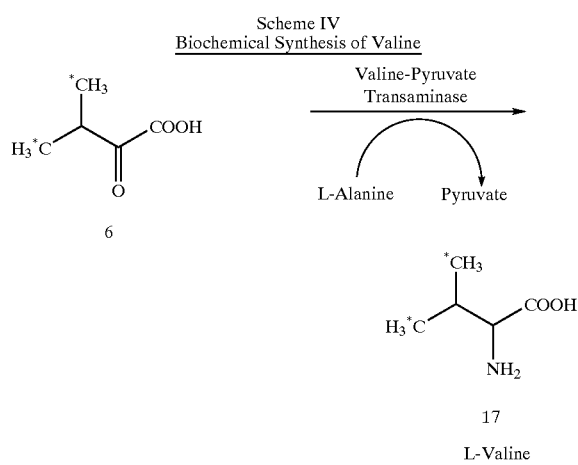

Means for preparing expression vectors that contain polynucleotide sequences coding specific polypeptides and for transforming host cells with those vectors are well known in the art. (See, for example R. W. Old, et al., *Techniques of Gene Manipulation*, Blackwell Science, London, 1994, and similar treatises in the field.) Likewise, methods for culturing the transformed cells to express the coded polypeptide and for isolating, purifying and re-folding the polypeptide are also well known in the art. Examples presented below describe the production of $^{13}$C-enriched samples of the 81–256 amino acid catalytic region of human stromelysin (SCD) from modified *E. coli*.

EXAMPLES

Example 1

Preparation of Uniformly $^{13}$C-Enriched Catalytic Domain of Human Stromelysin (SCD)

The 81-256 fragment (SEQ ID NO: 1) of stromelysin (SCD) is prepared by inserting a plasmid which codes for the production of the protein fragment into an *E. coli* strain and growing the genetically-modified bacterial strain in a suitable culture medium. The protein fragment is isolated from the culture medium, purified, and subsequently used in the two-dimensional NMR analysis of its affinity with test compounds in accordance with the method of this invention. The procedures for the preparation processes are described below.

Human skin fibroblasts (ATCC No. CRL 1507) are grown and induced using the procedure described by Clark, et al., *Archiv. Biochem. and Biophys.*, 241: 36 (1985). Total RNA is isolated from 1 g of cells using a RNAgents® Total RNA Isolation System Kit (Promega Corp., 2800 Woods Hollow Road, Madison, Wis. 53711, USA) following the manufacturer's instructions. A 1 μg portion of the RNA is denatured by heating at 80° C. for five minutes and then subjected to reverse transcriptase PCR using a GenAmp® RNA PCR kit (Applied Biosystems/Perkin-Elmer) following the manufacturer's instructions.

Nested PCR is performed using first primers (a) GAAAT-GAAGAGTCTTCAA (SEQ ID NO: 2) and (b) GCGTC-CCAGGTTCTGGAG (SEQ ID No. 3) and thirty-five cycles of 94° C., two minutes; 45° C., two minutes; and 72° C., three minutes. This is followed by re-amplification with internal primers (c) TACCATGGCCTATCCATTGGATG-GAGC (SEQ ID NO: 4) and (d) ATAGGATCCTTAGGTCT-CAGGGGA GTCAGG (SEQ ID NO: 5) using thirty cycles under the same conditions described immediately above to generate a DNA sequence coding for amino acid residues 1–256 of human stromelysin.

The PCR fragment is then cloned into PCR cloning vector pT7BIue® (Novagen, Inc.) according to the manufacturer's instructions. The resulting plasmid is cut with NcoI and BamHI and the stromelysin fragment is sub-cloned into the expression vector pET3d (Novagen, Inc.), again using the manufacturer's instructions.

A mature stromelysin expression construct coding for amino acid residues 81–256 plus an initiating methionine aminoacyl residue is generated from the 1–256 expression construct by PCR amplification. The resulting PCR fragment is first cloned into the pT7BIue® vector (Novagen, Inc.) and then sub-cloned into the pET3d vector (Novagen, Inc.), using the manufacturer's instructions in the manner described above, to produce plasmid pETST-83-256. This final plasmid is identical to that described by Qi-Zhuang, et al., Biochemistry, 31: 11231 (1992) with the exception that the present plasmid codes for a peptide sequence beginning two amino acids earlier, specifically at position 81, in the sequence of human stromelysin. Plasmid pETST-83-256 is transformed into E. coli strain BL21(DE3)/pLysS (Novagen, Inc.) in accordance with the manufacturer's instructions, to generate an expression strain, BL21(DE3)/pLysS/pETST-255-1.

A pre-culture medium is prepared by dissolving 1.698 g of $NaH_2PO_4 \cdot 7H_2O$, 0.45 g of $KH_2PO_4$, 0.075 g NaCl, 0.150 g $NH_4Cl$, 0.3 g U-$^{13}$C-glucose, 300 µl of 1 M aqueous $MgSO_4$ solution, and 15 ml of aqueous $CaCl_2$ solution in 150 ml of deionized water. The resulting solution of pre-culture medium is sterilized and transferred to a sterile 500 ml baffle flask. Immediately prior to inoculation of the pre-culture medium with the bacterial strain, 150 ml of a solution containing 34 mg/ml, of chloramphenicol in 100% ethanol and 1.5 ml of a solution containing 20 mg/ml of ampicillin is added to the flask contents. The flask contents are then inoculated with 1 ml of glycerol stock of genetically modified E. coli strain BL21(DE3)/pLysS/pETST-255-1. The flask contents are shaken (225 rpm) at 37° C. until an optical density of 0.65 is observed.

A fermentation nutrient medium is prepared by dissolving 113.28 g of $Na_2HPO_4 \cdot 7H_2O$, 30 g of $KH_2PO_4$, 5 g NaCl and 10 ml of 1% DF-60 antifoam agent in 9604 ml of deionized water. This solution is placed in a New Brunswick Scientific Micros Fermenter (Edison, N.J.) and sterilized at 121° C. for 40 minutes. Immediately prior to inoculation of the fermentation medium, the following pre-sterilized components are added to the fermentation vessel contents: 100 ml of a 10% aqueous solution of $NH_4Cl$, 15 g of uniformly $^{13}$C-enriched glucose, 20 ml of an aqueous 1 M solution of $MgSO_4$, 1 ml of an aqueous 1 M $CaCl_2$ solution, 5 ml of an aqueous solution of thiamin hydrochloride (10 mg/ml), 10 ml of a solution containing 34 mg/ml of chloramphenicol in 100% ethanol, and 1.9 g of ampicillin dissolved in the chloramphenicol solution. The pH of the resulting solution is adjusted to pH 7.00 by the addition of an aqueous solution of 4N $H_2SO_4$.

The pre-culture of E. coli strain BL21(DE3)/pLysS/pETST-255-1 from the shake flask scale procedure described above is added to the fermenter contents, and cell growth is allowed to proceed until an optical density of 0.48 is achieved. During this process, the fermenter contents are automatically maintained at pH 7.0 by the addition of 4N $H_2SO_4$ or 4N KOH as needed. The dissolved oxygen content of the fermenter contents is maintained above 55% air saturation through a cascaded loop which increased agitation speed when the dissolved oxygen content dropped below 55%. Air is fed to the fermenter contents at 7 standard liters per minute (SLPM) and the culture temperature is maintained at 37° C. throughout the process.

The cells are harvested by centrifugation at 17,000 ×g for 10 minutes at 4° C. and the resulting cell pellets are collected and stored at −85° C. The wet cell yield is 3.5 g/L. Analysis of the soluble and insoluble fractions of cell lysates by sodium dodecyl sulfate polyacrylamide gel electrophoresis (SDS-PAGE) reveals that approximately 50% of the stromelysin was found in the soluble phase.

The stromelysin fragment prepared as described above is purified employing a modification of the technique described by Ye, et al., Biochemistry, 31: 11231 (1992). The harvested cells are suspended in 20 mM Tris-HCl buffer (pH 8.0), sodium azide solution containing 1 mM $MgCl_2$, 0.5 mM $ZnCl_2$, 25 units/ml of Benzonase® enzyme (Benzon Pharma A/S Roskilde, Denmark), and an inhibitor mixture made up of 4-(2-aminoethyl)benzenesulfonyl fluoride ("AEBSF") Leupeptin®, Aprotinin® and Pepstatin® (all at concentrations of 1 mg/ml. AEBSF, Leupeptin®, Aprotinin®, and Pepstatin® are available from American International Chemical). The resulting mixture is gently stirred for one hour and then cooled to 4° C. The cells are then sonically disrupted using a 50% duty cycle. The resulting lysate is centrifuged at 14,000 rpm for 30 minutes and the pellet of insoluble fraction frozen at −80° C. for subsequent processing.

Solid ammonium sulfate is added to the supernatant to the point of 20% of saturation and the resulting solution loaded onto a 700 ml phenyl Sepharose fast flow ("Q-Sepharose FF) column (Pharmacia Biotech.). Prior to loading, the Sepharose column is equilibrated with 50 mM Tris-HCl buffer (pH 7.6 at 4° C.), 5 mM CaCl2, and 1 M $(NH_4)_2SO_4$. The loaded column is eluted with a linear gradient of decreasing concentrations of aqueous $(NH_4)_2SO_4$ (from 1 M down to 0 M) and increasing concentrations of aqueous $CaCl_2$ (from 5 mM to 20 mM) in Tris-HCl buffer at pH 7.6. The active fractions of eluate are collected and concentrated in an Amicon stirred cell (Amicon Inc.). The concentrated sample is dialyzed overnight in the starting buffer used with the Q-Sepharose FF column, 50 mM Tris-HCl (pH 8.2 at 4° C.) with 10 mM $CaCl_2$.

The dialyzed sample is then loaded on the Q-Sepharose FF column and eluted with a linear gradient comprising the starting buffer and 200 nM NaCl. The purified soluble fraction of the stromelysin fragment is concentrated and stored at 4° C. The pellet is solubilized in 8M guanidine-HCl. The solution is centrifuged for 20 minutes at 20,000 rpm and the supernatant added dropwise to a folding buffer comprising 50 mM Tris-HCl (pH 7.6), 10 mM $CaCl_2$, 0.5 mM $ZnCl_2$ and the inhibitor cocktail of AEBSF, Leupeptin (R) Aprotinin(R) and Pepstatin(R) (all at concentrations of 1

µg/ml). The volume of folding buffer is ten times that of the supernatant. The mixture of supernatant and folding buffer are centrifuged at 20,000 rpm for 30 minutes. The supernatant from this centrifugation is stored at 4° C. and the pellet subjected twice to the steps described above of solubilization in guanidine-HCl, refolding in buffer, and centrifugation. The final supernatants from each of the three centrifugations are combined and solid ammonium sulfate was added to the point of 20% saturation. The resulting solution thus derived from the insoluble fraction is subjected to purification on phenyl Sepharose and Q-Sepharose as described above for the soluble fraction. The purified soluble and insoluble fractions are combined to produce about 1.8 mg of purified stromelysin 81–256 fragment (SCD) per gram of original cell paste, uniformly enriched with $^{13}C$.

Example 2
Preparation of Specifically $^{13}C$-Enriched Catalytic Domain of Human Stromelysin (SCD)

SCD is expressed by culturing the BL21(DE3)/pLysS/pETST-255-1 modified *E. coli* strain in a medium comprising 2-keto-4-($^{13}C$)-butyric acid, or a salt thereof, and 2-keto-3-($^{13}C$-methyl)-4-($^{13}C$)-butyric acid, or a salt thereof. The methods used for preparation of the genetically-engineered strain of *E. coli*, and for expressing, isolating, and purifying the protein fragment are as described above, except for the use of U-$^{12}C$-glucose, instead of U-$^{13}C$-glucose.

It will be apparent to one of ordinary skill in the art that various modifications in the illustrated embodiments can be made without departing from the scope of the present invention.

We claim:

1. A compound of formula I

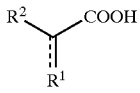

I or a salt thereof, wherein $R^1$ is oxygen or $NH_2$;

$R^2$ is selected from the group consisting of

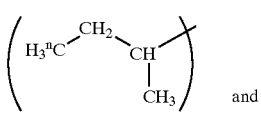

A and

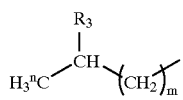

B wherein $R^3$ is hydrogen or $^nCH_3$;
the dotted line bond represents a second valence bond;
m is zero or one;
and n, at each occurrence, is 13 or 14; with the provisos that i) when $R^1$ is $NH_2$, the second valence bond represented by the dotted line bond to $R^1$ is absent and the hydrogen attached to the dotted line bond is present;

ii) when $R^1$ is oxygen, the second valence bond represented by the dotted line bond to $R^1$ is present and the hydrogen atom attached to the dotted line bond is absent;

iii) when $R^1$ is oxygen, $R^2$ is B and m is zero; and iv) when $R^1$ is $NH_2$, $R^3$ is hydrogen or $^nCH_3$.

2. A compound of formula Ia

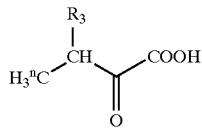

Ia or a salt thereof, wherein $R^3$ is hydrogen or $^nCH_3$ and n, at each occurrence is 13 or 14.

3. A compound according to claim 2 selected from the group consisting of:

2-keto-4-($^{13}C$)-butyric acid;

2-keto-3-($^{13}C$-methyl)-4-($^{13}C$)-butyric acid;

2-keto-4-($^{14}C$)-butyric acid; and 2-keto-3-($^{14}C$-methyl)-4-($^{14}C$)-butyric acid; or salts thereof.

4. A method of preparing a compound of formula Ia

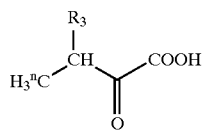

or a salt thereof, wherein $R^3$ is selected from the group consisting of hydrogen and $^nCH_3$, and n at each occurrence is 13 or 14, which comprises a) reacting a compound of formula IV

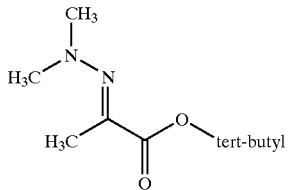

with isotopically-labeled methyl iodide ($H_3{}^nCI$) to produce a compound of formula V

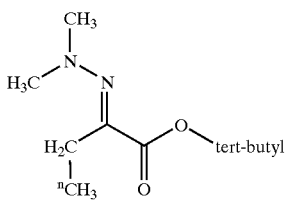

and b) removing the tert-butyl ester and dimethylhydrazino groups to produce 2-keto-4-($^nC$)-butyric acid.

5. A method according to claim 4, which further comprises salifying the reaction product of step b).

6. A method according to claim 4, which further comprises c) reacting the product of step b) with isotopically-labeled methyl iodide ($H_3{}^nCI$), where n is 13 or 14, to produce a compound of formula VI

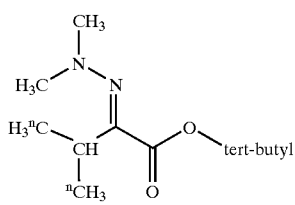

and d) removing the tert-butyl ester and dimethylhydrazino groups to produce 2-keto-3-($^nC$-methy 4-($^nC$)-butyric acid.

7. A method according to claim 6, which further comprises salifying the reaction product of step d).

* * * * *

SEQUENCE LISTING

```
<160> NUMBER OF SEQ ID NOS: 5

<210> SEQ ID NO 1
<211> LENGTH: 174
<212> TYPE: PRT
<213> ORGANISM: Artificial Sequence
<220> FEATURE:
<223> OTHER INFORMATION: 81-256 Catalytic region of human stromelysin

<400> SEQUENCE: 1

Phe Arg Thr Phe Pro Gly Ile Pro Lys Trp Arg Lys Thr His Leu Thr
1               5                   10                  15

Tyr Arg Ile Val Asn Tyr Thr Pro Asp Leu Pro Lys Asp Ala Val Asp
                20                  25                  30

Ser Ala Val Glu Lys Ala Leu Lys Val Trp Glu Glu Val Thr Pro Leu
            35                  40                  45

Thr Phe Ser Arg Leu Tyr Glu Gly Glu Ala Asp Ile Met Ile Ser Phe
    50                  55                  60

Ala Val Arg Glu His Gly Asp Phe Tyr Pro Phe Asp Gly Pro Gly Asn
65                  70                  75                  80

Val Leu Ala His Ala Tyr Ala Pro Gly Pro Gly Ile Asn Gly Asp Ala
                85                  90                  95

His Phe Asp Asp Asp Glu Gln Trp Thr Lys Asp Thr Thr Gly Thr Asn
            100                 105                 110

Leu Phe Leu Val Ala Ala His Glu Ile Gly His Ser Leu Gly Leu Phe
        115                 120                 125

His Ser Ala Asn Thr Glu Ala Leu Met Tyr Pro Leu Tyr His Ser Leu
    130                 135                 140

Thr Asp Leu Thr Arg Phe Arg Leu Ser Gln Asp Asp Ile Asn Gly Ile
145                 150                 155                 160

Gln Ser Leu Tyr Gly Pro Pro Asp Ser Pro Glu Thr Pro
                165                 170

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
gaaatgaaga gtcttcaa                                                 18
```

```
<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
gcgtcccagg ttctggag                                                 18

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
taccatggcc tatccattgg atggagc                                       27

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
ataggatcct taggtctcag gggagtcagg                                    30
```